US006898455B2

(12) United States Patent
Anderson et al.

(10) Patent No.: US 6,898,455 B2
(45) Date of Patent: *May 24, 2005

(54) METHOD FOR PROVIDING OPTIMAL DRUG DOSAGE

(75) Inventors: Carl M. Anderson, West Roxbury, MA (US); Steven Bradley Lowen, Burlington, MA (US); Perry F. Renshaw, Bedford, MA (US); Martin H. Teicher, Rye, NH (US); Luis C. Maas, III, San Francisco, CA (US)

(73) Assignee: The McLean Hospital Corporation, Belmont, MA (US)

( * ) Notice: Subject to any disclaimer, the term of this patent is extended or adjusted under 35 U.S.C. 154(b) by 284 days.

This patent is subject to a terminal disclaimer.

(21) Appl. No.: 10/162,529

(22) Filed: Jun. 3, 2002

(65) Prior Publication Data

US 2002/0193684 A1 Dec. 19, 2002

Related U.S. Application Data

(63) Continuation-in-part of application No. 09/430,209, filed on Oct. 29, 1999, now Pat. No. 6,400,978.

(51) Int. Cl.[7] ................................................. A61B 5/05
(52) U.S. Cl. ........................ 600/411; 600/407; 600/410; 600/419; 324/300
(58) Field of Search ................................. 600/407, 411, 600/410, 419; 324/300–318

(56) References Cited

U.S. PATENT DOCUMENTS

| | | | |
|---|---|---|---|
| 4,421,122 A | 12/1983 | Duffy | 128/731 |
| 4,435,449 A | 3/1984 | Stern | 424/330 |
| 4,502,007 A | 2/1985 | Mee et al. | 324/307 |
| 5,068,610 A | 11/1991 | Mehlkopf et al. | 324/312 |
| 5,142,231 A | 8/1992 | Jensen et al. | 324/309 |
| 5,270,651 A | 12/1993 | Wehrli | 324/308 |
| 5,307,015 A | 4/1994 | Kaufman et al. | 324/309 |
| 5,377,100 A | 12/1994 | Pope et al. | 364/410 |
| 5,655,531 A | 8/1997 | Nishimura et al. | 128/653 |
| 5,658,590 A | 8/1997 | Heiligenstein et al. | 424/464 |
| 5,671,741 A | 9/1997 | Lang et al. | 128/653 |
| 5,682,883 A | 11/1997 | Fiat | 128/632 |
| 5,696,168 A | 12/1997 | Heiligenstein et al. | 514/649 |
| 5,817,656 A | 10/1998 | Beasley, Jr. et al. | 514/220 |
| 6,258,032 B1 * | 7/2001 | Hammesfahr | 600/454 |
| 6,400,978 B1 * | 6/2002 | Teicher et al. | 600/410 |

OTHER PUBLICATIONS

Yufeng Zang, et al., "Objective Measurement of the Balance Dysfunction in Attention Deficit Hyperactivity Disorder Children", Chinese Journal of Clinical Rehabilitation, May 2002, vol. 6, No. 9, pp. 1372–1374.

"Attention–Deficit/Hyperactivity Disorder (ADHD): Prominent Striatal Abnormalities Revealed by Steady–State (MRI Relaxometry", M.H. Teicher et al., Abstract cited in Society for Neuroscience, vol. 24, 1998, paragraph 484.13, pp. 1238.

Dose–Dependent Effects of Methylphenidate on Activity, Attention, and Magnetic Resonance Measures in Children with ADHD, M.H. Teicher et al., Abstract cited in Society for Neuroscience, vol. 22, 1996, paragraph 468.3, pp. 1191.

"Methylphenidate Dose–Dependently Decreases Blood Flow in the Cerebellar Vermis of Children with ADHD", C. M. Anderson et al., McLean Hospital, Belmont, MA, NCDEU, poster presentation, June 1999.

(Continued)

*Primary Examiner*—Brian L. Casler
*Assistant Examiner*—William Jung
(74) *Attorney, Agent, or Firm*—Daly, Crowley, Mofford & Durkee, LLP

(57) ABSTRACT

A method for treating attention deficit/hyperactivity disorder (ADHD) includes performing an objective ADHD behavioral assay for a patient, administering a drug to the patient at varying doses, and performing an fMRI on the patient for the varying drug doses to determine an optimal dosage for the patient. The method can further include performing a further objective ADHD behavioral assay after the drug administration.

19 Claims, 10 Drawing Sheets

OTHER PUBLICATIONS

"Dose–Dependent Effects of Methylphenidate on Activity, Attention, and Magnetic Resonance Meausres in Children with ADHD", M. H. Teicher et al., McLean Hospital, Belmont, MA, poster presentation, Nov. 1998.

C. M. Anderson et al., "Childhood Abuse: Limbic System Checklist–33 and Cerebellar Vermis Blood Flow", Harvard Med. Sch., Developmental Biopsychiatry Research Program & The Brain Imaging Center, McLean Hospital, Belmont, MA, NR:384.

C. M. Anderson et al., "Cerebellar Vermis Blood Flow: Associations with Psychiatric Symptoms in Child Abuse and ADHD", Harvard Med. Sch., Developmental Biopsychiatry Research Program & The Brain Imaging Center, McLean Hospital, Belmont, MA, 655.4.

C. M. Anderson et al., Methylphenidate Dose—Dependently Decreases Blood Flow in the Cerebellar Vermis of Children with ADHD, Harvard Med. Sch., Developmental Biopsychiatry Research Program & The Brain Imaging Center, McLean Hosptial, Belmont, MA.

Jessie C. Anderson et al., "DSM–III Disorders in Preadolescent Children", Arch Gen Psychiatry, vol. 44, Jan. 1987, pp.69–76.

Hector R. Bird, et al., "Estimates of the Prevalence of Childhood Maladjustment in a Community Survey in Puerto Rico", Arch Gen Psychiatry, vol. 45, Dec.1998,pp. 1120–1126.

Peter Szatmari et al., "Ontario Child Health Study: Prevalence of Attention Deficit Disorder with Hyperactivity", Child Psychol. Psychiat. vol. 30, No. 2, 1989, pp. 219–230.

Russell A. Barkley, Ph.D., "A Critique of Current Diagnostic Criteria for Attention Deficit Hyperactiivity Disorder: Clinical and Research Implications", Developmental and Behavioral Pediatrics, vol. 11, No. 6, Dec. 1990, pp. 343–352.

Warren W. Tryon, "The Role of Motor Excess and Instrumented Activity Measurement in Attention Deficit Hyperactivity Disorder", Behavior Modification, vol. 17, No. 4, Oct. 1993, pp. 371–406.

Helen Orvaschel, Ph.D., Schedule for Affective Disorder and Schizophrenia for School–Age Children Epidemiologic Version, Kiddie–SADS–E (K–SADS–E), Orvaschel & Puig–Antich, Fifth Revision, Feb. 1994, pp. 1–128.

S. Ogawa et al., "On The Characteristics Of Functional Magnetic Resonance Imaging Of The Brain", Annu. Rev. Biophys. Biomol. Struct. 1998. 27 pp 447–474.

Linus Pauling et al., "The Magnetic Properties And Structure Of Hemoglobin, Oxyhemoglobin And Carbonmonoxyhemoglobin", Chemistry: Pauling and Coryell, vol. 22, Mar. 1936, pp. 210–216.

M. H. Teicher et al., "Attention–Deficit/Hyperactviity Disorder (ADHD): Prominent Striatal Abnormalitites Revealed by Steady–State fMRI Relaxometry", Developmental Biopsychiatry Research Program and Neuroimaging Center, McLean Hospital, Belmont, MA, NR:384.

Seymour S. Kety, "Measurement of Local Blood Flow By The Exchange Of An Inert, Diffusible Substance", Peripheral Blood Flow Measurement , Methods in Medical Research, vol. 8, 1960, pp. 228–235.

Peter C.M. van Zijl et al., "Quantitative Assessment of Blood Flow, Blood Volume And Blood Oxygenation Effects In Functional Magnetic Resonance Imaging", Nature Medicine, vol. 4, No. 2, Feb. 1998, pp. 159–167.

Mark A. Goldberg et al., "Value of T1 and T2 Relaxation Times From Echoplanar MR Imaging In The Characterization Of Focal Hepatic Lesions", AJR 1993; 160 pp. 1011–1017.

Hans C. Lou et al., "Focal Cerebral Hypoperfusion In Children With Dysphasia And/Or Attention Deficit Disorder", Arch Neurol, vol. 41, Aug 1984, pp. 825–829.

Hans C. Lou et al., "Striatal Dysfunction In Attention Deficit And Hyperkinetic Disorder", Arch Neurol, vol. 46, Jan. 1989, pp. 48–52.

Monique Ernst, et al., "Reduced Brain Metabolism In Hyperactive Girls", J. Am. Acad. Child Adolesc. Psychiatry, 33:6, Jul./Aug. 1994, pp. 858–868.

Monique Ernst, et al., "DOPA Decarboxylase Activity In Attention Deficit Hyperactivity Disorder Adults. A [Fluorine–18] Fluorodopa Positron Emission Tomographic Study", The Journal of Neuroscience, Aug. 1, 1998, 18(15), pp. 5901–5907.

Ann M. Graybiel, et al., "The Basal Ganglia And Adaptive Motor Control", Science, vol. 265, Sep. 23, 1994, pp. 1826–1830

Chandan J. Vaidya et al., "Selective Effects Of Methylphenidate In Attention Deficit Hyperactivity Disorder: A Functional Magnetic Resonance Study", Proc. Natl Acad. Sci. vol. 95, Nov. 1998, pp. 14494–14499.

Nora D. Volkow et al., "Effects of Methylphenidate On Regional Brain Glucose Metabolism In Humans: Relationship To Dopamine $D_2$ Receptors", Am J Psychiatry 154:1, Jan. 1997, pp. 50–55.

Martin H. Teicher, et al., "Objective Measurement of Hyperactivity and Attentional Problems in ADHD", J. Am. Acad. Child Adolesc. Psychiatry, 35:3, Mar. 1996, pp. 334–342.

Martin P. Paulus et al., "The Effects of MDMA and Other Methylenedioxy–Substituted Phenylalkylamines on the Structure of Rat Locomotor Activity", Neuropsychopharmacology 1992, vol. 7, No. 1, pp. 15–31.

Luis C. Maas, et al., "Decoupled Automated Rotational and Translational Registration for Functional MRI Time Series Data: The DART Registration Algorithm", MRM 1997, 37, pp. 131–139.

"Society of Magnetic Resonance in Medicine"; Book of Abstracts, vol. I; Tenth Annual Scientific Meeting and Exhibition; Aug. 10–16, 1991; San Francisco, CA; pp.107.

* cited by examiner

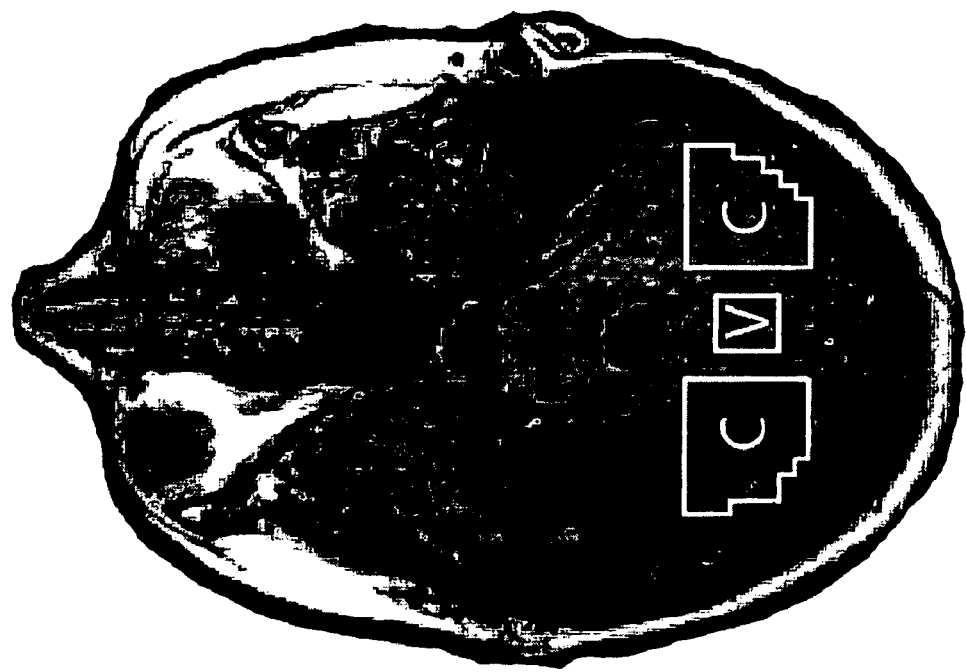
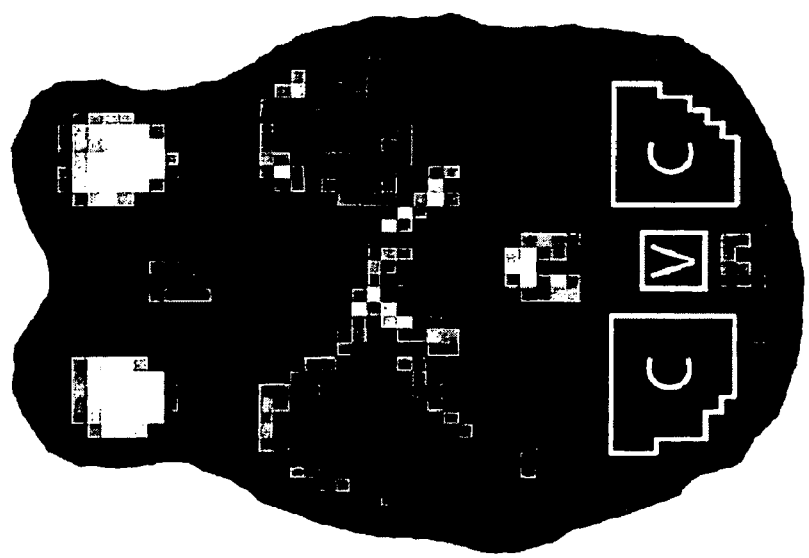
FIG. 7B
FIG. 7A

METHOD FOR PROVIDING OPTIMAL DRUG DOSAGE

CROSS REFERENCE TO RELATED APPLICATIONS

This application is a continuation-in-part of U.S. application Ser. No. 09/430,209 filed on Oct. 29, 1999, now U.S. Pat. No. 6,400,978 which is incorporated herein by reference.

STATEMENT REGARDING FEDERALLY SPONSORED RESEARCH

This work was sponsored by NIMH grants MH-48343, MH-53636, and NIDA Grants DA-09448 and DA-14178. The government may have certain rights in this invention.

FIELD OF THE INVENTION

This invention relates to methods of measuring nuclear magnetic resonance characteristics of nuclei generally, and, in particular to a method of determining the spin-spin relaxation time (T2) of nuclei using spin echoes and for utilizing the T2 relaxation time to aid in detection of mental disorders including but not limited to attention-deficit/hyperactivity disorder (ADHD). This invention also relates to determining an optimal drug dosage for treating disorders.

BACKGROUND OF THE INVENTION

As is known in the art, magnetic resonance imaging (MRI) (aka nuclear magnetic resonance or NMR) is a form of medical imaging in which the data is displayed as images which are presented in the form of individual slices that represent planar sections of objects. The data in the images represents the density and bonding of protons (primarily in water) in the tissues of the body, based upon the ability of certain atomic nuclei in a magnetic field to absorb and re-emit electromagnetic radiation at certain frequencies.

As is also known, MRI is based on the magnetic properties of atomic nuclei with odd numbers of protons or neutrons, which exhibit magnetic properties because of their spin. The predominant source of magnetic resonance signals in the human body is hydrogen nuclei or protons. In the presence of an external magnetic field these hydrogen nuclei align along the axis of the external magnetic field and can precess or wobble around that field direction at a definite frequency known as the Larmor frequency.

The magnetic resonance effects occur when nuclei in a static magnetic field H are excited by a rotating magnetic field H1 in the x, y plane resulting in a total vector M given by M=Hz+H1(xcos w0t+y sin w0t). Upon cessation of the excitation, the magnetic field decays back to its original alignment with the static field H, emitting electromagnetic radiation at the Larmor frequency which can be detected by the same coil which produced the excitation.

One method for imaging utilizes a transmit/receive coil to emit a magnetic field at frequency $f_0$ which is the Larmor frequency of plane P. Subsequently, magnetic gradients are applied in the y and x directions $G_x$, $G_y$ for times $t_x$, $t_y$. A signal is detected in a data collection window over the period of time for which a magnetic gradient $G_x$ is applied.

The detected signal $S(t_x, t_y)$ can be expressed as a two-dimensional Fourier transform of the magnetic resonance signal s(x,y) with $u=\gamma G_x t_x/2\pi$, $v=\gamma G_y t_y/2\pi$. The magnetic resonance signal s(x,y) depends on the precise sequence of pulses of magnetic energy used to perturb the nuclei.

For a typical sequence known as spin-echo the detected magnetic resonance signal can be expressed $$s(x,y)=\rho(1-e^{-t/T1})(e^{-t/T2})$$

where $\rho$ is the proton density, and T1 (the spin-lattice decay time) and T2 (the spin-spin decay time) are constants of the material related to the interactions of water in cells. Typically T1 ranges from 0.2 to 1.2 seconds, while T2 ranges from 0.05 to 0.15 seconds.

By modification of the repetition and orientation of excitation pulses, an image can be made T1, T2, or proton density dominated. A proton density image shows static blood and fat as white and bone as black, while a T1 weighted image shows fat as white, blood as gray, and cerebrospinal fluid as black and T2 weighted images tend to highlight pathology since pathologic tissue tends to have longer T2 than normal tissue.

To measure spin-spin decay or relaxation time ($T_2$) a technique referred to as the spin echo technique was developed. The spin-echo technique includes the steps of applying an RF pulse sequence at the Larmor frequency of the nuclei, whose T2 is being measured. The first RF pulse is sufficient duration to force the net magnetic moment of the nuclei to rotate 90°. This is followed by one or more RF pulses at the same Larmor frequency of sufficient duration to rotate the net magnetic field 180°. After each 180° pulse a signal referred to as a "spin-echo signal" is produced. The T2 relaxation time of the nuclei is indicated by the curve drawn through the points of maximum amplitude of the echo signals received.

This technique would produce an accurate measurement of T2 if the RF magnetic field was uniform at the same Larmor frequency because then only one spin-echo signal would be generated with each 180° pulse. Unfortunately, the RF magnetic field is not uniform. For example, some portions of the RF field may be at the Larmor frequency but other portions may be at a higher or lower frequency. It is believed that as a result of this, the inhomogeneities in the RF magnetic field produce so-called "stimulated echos" in addition to the primary echos.

In the present practice of the spin-echo technique for measuring T2, after the 90° pulse, the first 180° pulse occurs after a time period, usually called "tau." Stimulated echos, however, can appear at these same times and when they do, they will be masked by and mingled with the primary echos. As a result, the degree of error in the measured T2 is unknown. Because of the errors caused by inhomogeneities in the static and RF magnetic fields of NMR machines, it is thus not possible to directly measure the T2 relaxation time (T2 RT) with a reasonable degree of certainty or accuracy.

SUMMARY OF THE INVENTION

As is also known in the art, conventional Blood Oxygenation Level Dependent (BOLD) functional MRI (fMRI) is a technique which utilizes the paramagnetic properties of deoxyhemoglobin for observing dynamic brain activity changes between baseline and active conditions.

It has been recognized in accordance with the present invention that one problem with the BOLD technique is that the mismatch between blood flow and oxygen extraction that occurs as an acute reaction to enhanced neuronal activity in BOLD does not persist under steady state conditions. Instead, regional blood flow is regulated to appropriately match perfusion with ongoing metabolic demand and deoxyhemoglobin concentration becomes constant between regions in the steady-state.

It has also been recognized in accordance with the present invention that to delineate effects of chronic drug treatment on basal brain function and to detect other conditions, it is necessary to identify possible resting or steady-state differences in regional perfusion between groups of subjects. Thus, one problem with the BOLD technique is that it cannot be used to provide insight into possible resting or steady-state differences in regional perfusion between groups of subjects, or to delineate effects of chronic drug treatment on basal brain function.

Because regional blood flow is regulated to appropriately match perfusion with ongoing metabolic demand and deoxyhemoglobin concentration becomes constant between regions in the steady-state, this indicates that regions with greater continuous activity would be perfused at a greater rate, and these regions would receive, over time, a greater volume of blood and a greater number of deoxyhemoglobin molecules per volume of tissue. Thus, there should be an augmentation in the paramagnetic properties of the region which is not detectable using the BOLD technique. Such augmentation in the paramagnetic properties of the region should be detectable as a diminished T2 relaxation time.

It has thus been further recognized in accordance with the present invention that it would be desirable to be able to identify possible resting or steady-state differences in regional perfusion between groups of subjects since such identification may provide an aid to diagnose or to directly diagnose different medical conditions.

For example, attention-deficit hyperactivity disorder (ADHD) is a highly heritable and prevalent neuropsychiatric disorder estimated to affect 6% of school-age children. Clinical hallmarks are inattention, hyperactivity and impulsivity, which often respond dramatically to treatment with methylphenidate or dextroamphetamine. Etiological theories postulate a deficit in corticostriatal circuits, particularly those components modulated by dopamine. Neuroanatomical studies have also implicated the cerebellum, a brain region involved in motor control, in the pathology of ADHD. ADHD is typically diagnosed by subjective observation of symptoms (e.g. inattention, hyperactivity and impulsivity) in a subject.

It would, therefore, be desirable to provide technique for reliably measuring the T2 RT. It would also be desirable to provide a technique for non-invasively diagnosing ADHD with MRI. It would be further desirable to reliably measure T2 RT in a particular region of interest and to use the T2 RT to aid in diagnosing and monitoring a disease. It would be still further desirable to provide a technique to measure T2 RT and to correlate changes in T2 RT to changes in blood flow.

Thus, in accordance with the present invention, an MRI system for measuring the T2 relaxation time of a sample, includes a magnet system for generating a steady, uniform magnetic field and for generating magnetic field gradients in an examination space adapted to receive the sample, a magnet controller for controlling the magnet system, an RF transmitter and receiver for generating and detecting spin resonance signals, a sampling device for sampling the detected spin resonance signals generated and a processor for computing a T2 relaxation time (RT) in one or more regions of interest (ROI) using median values for each of the detected spin resonance signals in the ROI.

With this particular arrangement, a system for identifying possible resting or steady-state differences in regional perfusion between groups of subjects is provided. By being able to identify resting or steady-state differences in regional perfusion between groups of subjects, the system can be used to aid in the diagnosis of or to directly diagnose different conditions in subjects. For example by reliably measuring the T2 RT in a particular region of interest in a subject it may be possible to provide a non-invasive technique for assisting in the diagnoses of a variety of diseases including but not limited to ADHD, Asperger's syndrome, Autism, substance abuse disorders, seasonal affective disorder, childhood sexual abuse, schizophrenia, manic depression, Alzheimer's disease, Parkinson's disease and compulsive disorders.

In accordance with a further aspect of the present invention, a method for determining a T2 relaxation time in a sample includes the steps of (a) obtaining one or more T*1 matched axial images through a predetermined number of axial planes of the sample, (b) obtaining one or more spin echo, echoplanar image sets, with TE incremented by a predetermined value in each consecutive image set through the same axial planes used in step (a), (c) generating a map of T2 for each of the T*1 matched axial images, (d) identifying one or more regions of interest (ROI) in the images of the sample, (e) computing the median pixel intensity values in the ROI and (f) determining a T2 relaxation time from the median pixel values.

With this particular arrangement, a technique for accurately determining a T2 RT using median values in a region of interest is provided. Median values give better estimates for T2 because they are less heavily influenced by partial volume effects (e.g. having a voxel with increased CSF content does not bias the median T2 estimate in the way that the mean T2 estimate would be increased). CSF T2 values are much higher than those of brain tissue. Thus, using the median value to compute the T2 RT, a better estimate of T2 RT is provided.

In one embodiment, 32 separate spin echo images, with TE incremented by 4 msec in each consecutive image set (e.g. TE (1)=32 msec, TE (2)=36 msec, . . . TE (32)=160 msec) are collected. Each echo is generated following a single 90° pulse-tau 180° pulse-tau pulse sequence. The time 2 tau is the time to echo (TE) and it is this value which is stepped. This approach results in a technique which provides relatively sensitive measurements of T2 RT. Thus this technique allows comparisons of relatively small changes in T2 RT to be made.

Importantly, by comparing T2 RT values it has been found that changes in T2 values can be correlated to changes in blood flow. Such correlation has a variety of applications. For example, if a drug administered to a patient leads to changes in blood flow, such changes can be detected by detecting changes in T2 RT. Thus the technique of the present invention can be used to actually detect changes in T2 RT which correlate with changes in blood flow. Thus, the technique of the present invention can be used to monitor changes in a patient. That is, the technique of the present invention can be used to determine or monitor in an objective sense, whether therapy improves conditions in a subject.

It should, therefore, be appreciated that in one aspect of the invention it has been recognized that changes in T2 RT can correlate with changes in blood flow. Such correlation can be made using any technique which provides a relatively sensitive measurement of T2 RT. In another aspect of the present invention, a technique for obtaining a relatively sensitive measurement of T2 RT has been found.

It has not been possible, heretofore, to detect changes in T2 RT and relate or correlate such changes in T2 RT to changes in blood flow. Moreover, the prior art indicates that it is not believed possible that changes in measured values of T2 RT could be related or correlated to changes in blood flow.

In accordance with the present invention, however, studies which included measurements of baseline T2 RT values and test T2 RT values as well as comparisons between baseline T2 RT and test T2 RT values revealed a correlation between T2 RT values and changes in blood flow of test subjects.

In accordance with a still further aspect of the present invention, apparatus for aiding the detection of ADHD in a subject includes (a) a system for exposing the subject to one or more pulses of electromagnetic energy so as to cause a time-varying response in the subject, (b) a detector for detecting in the subject a response to each of the one or more pulses of electromagnetic energy and (c) a T2 RT processor for receiving the responses and for computing a T2 relaxation time and for providing an output such that the computed T2 relaxation time can be compared with a reference T2 relaxation time such that a determination can be made as to whether the subject has ADHD.

With this particular arrangement, an apparatus for indirectly assessing blood volume in the striatum (caudate and putamen and cerebellum) under steady-state conditions and for non-invasively diagnosing ADHD is provided. In a study using the apparatus, it was found that boys with ADHD had higher T2 relaxation time (T2 relaxometry) measures in putamen bilaterally than healthy controls. In one study eleven boys with ADHD had higher T2 relaxation times than six non-ADHD boys. The probability of this occurring by chance is 0.8%. The relaxation times correlated with the child's capacity to sit still, and their accuracy in performing a computerized attention task. Product-moment correlation coefficients (denoted r) for each of the above activities as well as with a probability of finding this occurrence by chance (denoted p) were computed using conventional techniques. The computations of r and p resulted in values of $r=-0.73$, $p<0.001$ and $r=-74$, $p<0.001$ respectively. Blinded, placebo-controlled daily treatment with methylphenidate significantly altered relaxation times in the putamen of children with ADHD ($p=0.006$), and dose-dependently altered relaxation times in the cerebellum in eight of the most hyperactive boys ($F_{3,21}=5.011$, $p=0.0089$) though the magnitude and direction of the effect was strongly dependent on the child's unmedicated activity state. No differences between ADHD children and controls in caudate or thalamus were observed, nor did relaxation times in these regions change with methylphenidate. It was discovered that ADHD symptoms may be closely tied to functional abnormalities in the putamen and cerebellum which are predominantly involved in the regulation and coordination of motoric behavior. While in this particular study the putamen was found to correspond to a brain region useful for diagnosing ADHD, it should be appreciated that other brain regions may be useful for diagnosing ADHD such as the cerebellum or frontal cortex. It should also be appreciated that the apparatus and technique of the present invention may be equally applied to other brain regions (or even other organs) and may be useful for diagnosing conditions other than ADHD.

In accordance with a yet further aspect of the present invention, a method for aiding the detection of ADHD in a subject including the steps of (a) subjecting the subject to one or more pulses of electromagnetic energy so as to cause a time-varying response in the subject, (b) computing a relaxation time T2 of the time varying response in the subject, wherein median values of the time varying response in the subject are used to compute the relaxation time T2 and providing an output which can be used to compare the detected relaxation time T2 with a reference relaxation time T2 such that a determination can be made as to whether the subject has ADHD.

With this particular arrangement, a technique for non-invasively diagnosing ADHD by indirectly assessing blood volume in the striatum (caudate and putamen) and cerebellum under steady-state conditions is provided.

In another aspect of the invention, a method for treating a disorder, such as attention deficit/hyperactivity disorder (ADHD), includes performing an objective ADHD behavioral assay for a patient, administering a drug to the patient at varying doses, and performing an fMRI on the patient for the varying drug doses to determine an optimal dosage for the patient.

BRIEF DESCRIPTION OF THE DRAWINGS

The foregoing features of the invention, as well as the invention itself may be more fully understood from the following detailed description of the drawings, in which:

FIG. 7A is a matched T1-weighted axial image of a brain showing regions of interest for determining optimal drug dosage in accordance with the present invention;

FIG. 7B is a T2-RT axial image of a brain showing regions of interest for determining optimal drug dosage in accordance with the present invention;

DETAILED DESCRIPTION OF THE INVENTION

Before providing a detailed description of the present invention, it should be understood that although reference is sometimes made herein to providing output to aid in the detection of ADHD, the techniques of the present invention can be equally applied to aid in the detection of a variety of conditions or diseases other than ADHD. Reference is also made herein to computation of T2 RT for a particular region of the brain (i.e. the putamen) and that such T2 relaxation time (RT) computations for the putamen aid in the detection of ADHD. It should also be understood that the apparatus and techniques of the present invention are not limited to computation of T2 RT in the putamen nor to diagnosis of ADHD. It is recognized herein that the techniques of the present invention may be applied to other brain regions and that examination of T2 RT in other brain regions may be useful to aid in diagnosing ADHD and/or conditions other than ADHD. It should also be appreciated that the techniques of the present invention may also be applied to organ base methodologies.

Generally, the system described herein provides an apparatus for identifying possible resting or steady-state differences in regional perfusion between groups of subjects. By being able to identify resting or steady-state differences in regional perfusion between groups of subjects, the apparatus and techniques of the present invention can be used to aid in the diagnosis of or to directly diagnose a variety of different conditions in subjects. For example, by reliably measuring the T2 RT in a particular region of interest in a subject it may be possible to provide a non-invasive technique for assisting in the diagnoses of a variety of diseases including but not limited to ADHD, Asperger's syndrome, Autism, substance abuse disorders, seasonal affective disorder, childhood sexual abuse, schizophrenia, manic depression, Alzheimer's disease, Parkinson's disease and compulsive disorders.

Figure 1:
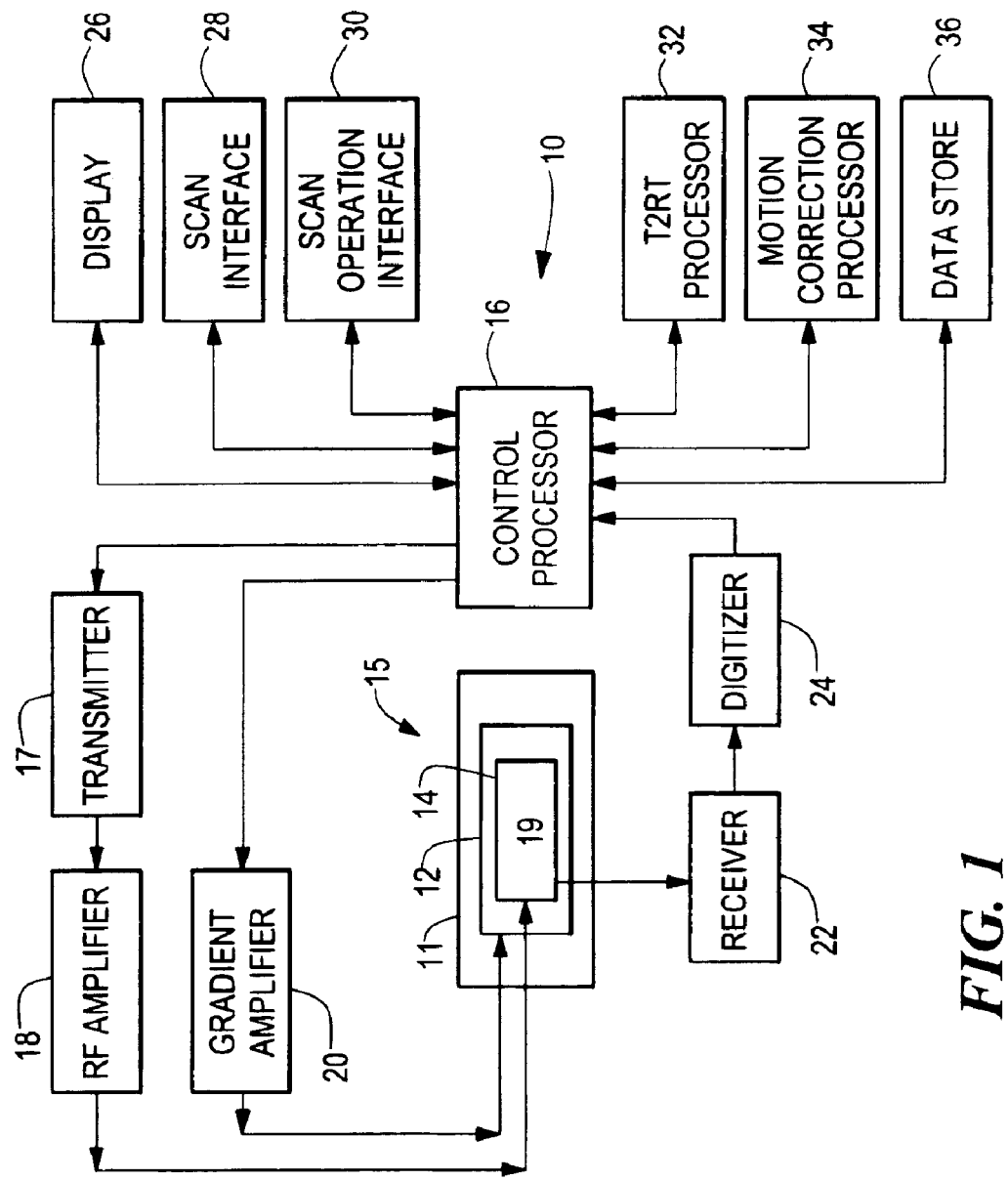
FIG. 1 is a block diagram of a magnetic resonance imaging system.

Turning now to FIG. 1, a magnetic resonance imaging (MRI) system 10 that may be programmed to non-invasively aid in the diagnosis of attention-deficit/hyperactivity disorder (ADHD) and other conditions in accordance with the present invention includes a magnet 11 having gradient coils 12 and RF coils 14 disposed thereabout in a particular manner to provide a magnet system 15. In response to control signals provided from a controller processor 16, a transmitter 17 provides a transmit signal to the RF coil 14 through an RF power amplifier 18. A gradient amplifier provides a signal to the gradient coils 12 also in response to signals provided by the control processor 16.

The magnet system 15 is driven by the transmitter 17 and amplifiers 18, 20. The transmitter 17 generates a steady magnetic field and the gradient amplifier 20 provides a magnetic field gradient which may have an arbitrary direction. For generating a uniform, steady magnetic field required for MRI, the magnet system 10 may be provided having a resistance or superconducting coils and which are driven by a generator. The magnetic fields are generated in an examination or scanning space or region 19 in which the object to be examined is disposed. For example, if the object is a person or patient to be examined, the person or portion of the person to be examined is disposed in the region 19.

The transmitter/amplifier 17,18 drive the coil 14. After activation of the transmitter coil 14, spin resonance signals are generated in the object situated in the examination space 19, which signals are detected and are applied to a receiver 22. Depending upon the measuring technique to be executed, the same coil can be used for the transmitter coil and the receiver coil or use can be made of separate coils for transmission and reception. The detected resonance signals are sampled, digitized in a digitizer 24. Digitizer 24 converts the analog signals to a stream of digital bits which represent the measured data and provides the bit stream to the control processor 16.

The control processor 16 processes the resonance signals measured so as to obtain an image of the excited part of the object. A display 26 coupled to the control processor 16 is provided for the display of the reconstructed image. The display 26 may be provided for example as a monitor, a terminal, such as a CRT or flat panel display.

A user provides scan and display operation commands and parameters to the control processor 16 through a scan interface 28 and a display operation interface 30 each of which provide means for a user to interface with and control the operating parameters of the MRI system 10 in a manner well known to those of ordinary skill in the art.

The control processor 16 also has coupled thereto a T2 RT processor 32, an optional motion correction processor 34 and a data store 36. Each of the components depicted in FIG. 1, except for the T2 RT processor 32 and the motion correction processor 34 are standard equipment in commercially available magnetic resonance imaging systems. It should be appreciated that the MRI system must be capable of acquiring the data which is used by the T2 RT processor 32. In some embodiments, the T2 RT processor 32 may be provided as a general purpose processor or computer programmed in accordance with the techniques described herein to compute T2 RT. For example, in some applications it may be desirable to provide a single processor or computer which is appropriately programmed to perform the functions of control processor 16, T2 RT processor 32 and motion correction processor 34. In other embodiments, T2 RT processor 32 and/or motion correction processor 34 may be provided as specially designed processors (e.g. digital signal processors) or other specially designed circuits. In any event T2 RT processor 32 is unique in that it is programmed or otherwise designed to acquire and analyze data to aid in the detection of ADHD and other diseases in accordance with the present invention as described below.

The T2 RT processor 32 and motion correction processor 34 (when needed) cooperate to compute T2 relaxation values. One particular technique for determining T2 RT values is described below in conjunction with FIG. 2. Suffice it here to say that once MRI images which have been corrected for motion via processor 34 are displayed on the display 26, one or more regions of interest are identified on the image. The regions of interest can be identified using a variety of techniques including empirical and analytical techniques. For example, image processing techniques can be used to identify particular regions within the image (in this case it may not be necessary to display the image). Alternatively a CAD system can be used to circumscribe the one or more regions of interest on an image viewable on the display 26.

Once the region of interest has been found, the T2 RT processor 32 computes the median value of all designated pixels within an ROI. It has been found that the median value of all designated pixels within an ROI provides a regional estimate less susceptible to contamination by spurious values from bordering white matter and cerebrospinal fluid regions than the mean value. T2 RT processor 32 then determines regional T2 relaxation time from the median value of all the designated pixels. In one particular embodiment, a linear least squares regression technique is used to determine T2 relaxation time. The results of the T2 RT processor can be displayed in the display 26 and used to aid in the diagnosis of disorders including but not limited to ADHD.

Figure 2:
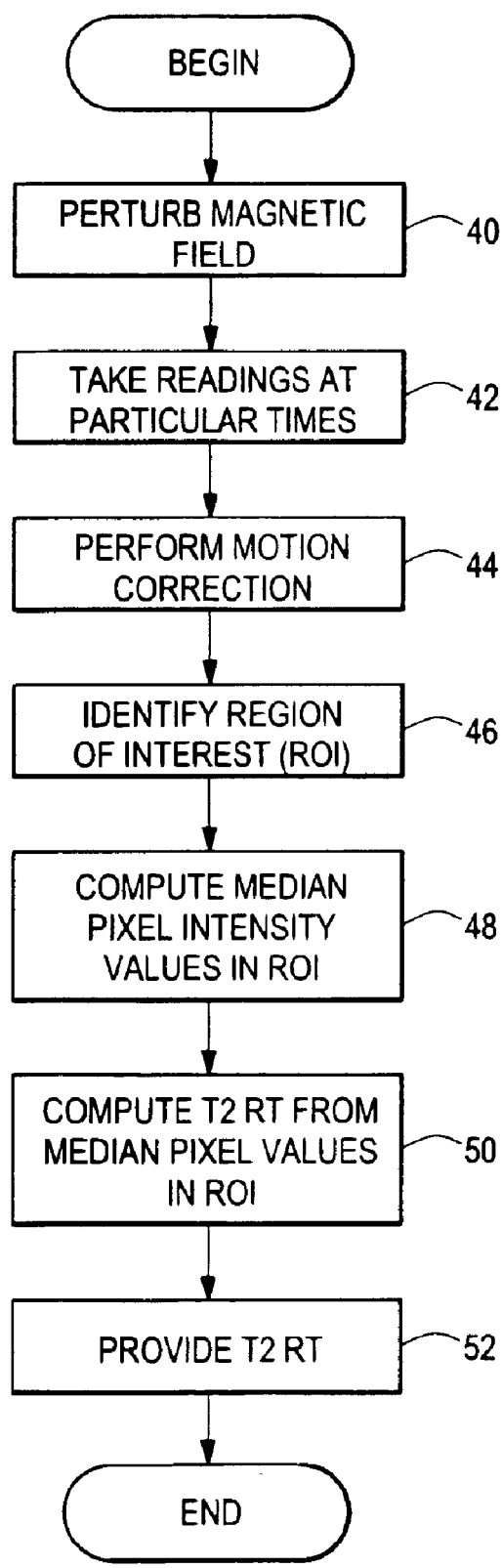
FIG. 2 is a flow diagram of the steps performed to compute a T2 relaxation time.

Referring now to FIG. 2, a flow diagram shows the processing performed by a processing apparatus which may, for example, be provided as part of an MRI system such as that shown in FIG. 1 to determine T2 RT. The rectangular elements in the flow diagram are herein denoted "processing blocks" and represent computer software instructions or groups of instructions. The diamond shaped elements in the flow diagrams are herein denoted "decision blocks" and represent computer software instructions or groups of instructions which affect the processing of the processing blocks.

Alternatively, the processing blocks represent steps performed by functionally equivalent circuits such as a digital signal processor circuit or an application specific integrated circuit (ASIC). It should be appreciated that some of the steps described in the flow diagram may be implemented via computer software while others may be implemented in a different manner e.g. via an empirical procedure. The flow diagrams do not depict the syntax of any particular programming language. Rather, the flow diagrams illustrates the functional information one of ordinary skill in the art requires to fabricate circuits or to generate computer software to perform the processing required of the particular apparatus. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention.

Turning now to FIG. 2, processing begins in steps 40 and 42 in which after positioning subjects to be tested (e.g. children or other persons possibly having brain dysfunction) in a scanning region of an MRI system of the type described above in conjunction with FIG. 1, and instructing the subjects to remain as still as possible, images of particular regions of interest (ROI) are acquired by perturbing the magnetic field in the subject and taking readings at particular times. In one particular embodiment, the images are acquired using a 1.5-T magnetic resonance scanner of the type manufactured by Signa, General Electric Medical Systems, Milwaukee, Wis. equipped with a whole-body, resonant gradient set capable of echo planar imaging (Advanced NMR Systems, Inc., Wilmington, Mass.), and a standard quadrature head coil for image detection.

During each examination, three categories of images are obtained. The first category of images correspond to scout images (typically T1-weighted sagittal images) which are obtained to use as a guide to determine the region of the brain which is being viewed. The second category of images correspond to T*1 matched axial images taken through a predetermined number of planes for which maps of T2 are generated. The T*1 matched images typically have a relatively high resolution (e.g. on the order of 1 mm×1 mm or better). Relatively low resolution images are typically not preferred since it becomes more difficult with such low resolution images to identify relatively small brain structures. The third category of images correspond to a predetermined number of spin echo, echoplanar image sets, with time to echo or echo time (TE) incremented by a predetermined amount in each consecutive image set through the same axial planes. The data from which the images are provided can be stored in either a permanent or a temporary storage device.

In one particular embodiment, maps of T2 are generated from T*1 matched axial images through ten planes and thirty-two spin echo, echoplanar image sets, with TE incremented by 4 msec in each consecutive image set (e.g. TE (1)=32 msec, TE (2)=36 msec, . . . TE (32)=160 msec) through the same ten axial planes. Those of ordinary skill in the art will appreciate that any number of planes in the range of about 1–40 planes can be used and that any number of spin-echo echoplanar image sets in the range of about 16–48 sets can be used. It should be appreciated that while estimates of T2 derived from 16 to 48 echoes will provide relatively accurate results, a number of echoes outside that range may be used. It should be appreciated that estimates of T2 derived from smaller numbers of echoes will tend to be less accurate. Also, the time to repeat or repetition time (TR) is selected having a value in the range of about 5–15 msec with about 10 msec being preferred and the slice thickness is selected to be in the range of about 3 mm to about 11 mm with 7 mm being preferred with a 3 mm skip.

It should be appreciated that these values produced accurate results with the above-mentioned MR scanner and head coil but that other values may be used especially if different hardware is used. Also, the system is provided having an in-plane resolution of about 3.125 mm×3.125 mm with a field of view (FOV) typically of about 200 mm. It should be appreciated that each of the above values and ranges of values are representative and that other values other than the values or ranges described above may also produce accurate results. The above values and ranges were found to produce accurate results with the above-mentioned MR system.

Next, as shown in step 44, if necessary the TE-stepped images are corrected for in plane motion. Such correction can be accomplished for example, by transferring the images to an offline workstation and using an image registration technique. In this particular embodiment, a modification of the Decoupled, Automated Rotational and Translational (DART) image registration technique is used.

The DART technique is described in Decoupled, Automated Rotational and Translational Registration for Functional MRI Time Series Data; The DART Registration Algorithm, Magnetic Resonance in Medicine 1997; 37:131–139 and is also described in U.S. Pat. No. 5,850,486 issued Dec. 15, 1998 assigned to the assignee of the present invention. Both of the aforementioned references are hereby incorporated by reference. Those of ordinary skill in the art will appreciate of course that other conventional image registration techniques can also be used.

For registration of high-contrast time-varying MRI data as might be seen in T2-mapping or CBV-mapping experiments of the type performed in conjunction with the ADHD studies described herein, the following techniques were used to modify the above-mentioned DART technique.

The basic DART assumes that the underlying images are the same, just rotated and translated. When this is not true, a "bias" is introduced into the estimates of the respective parameters. The goal of the modification of the DART technique mentioned above, is to first estimate the "bias" based on a model of the registered data, and then correct the true data taking this estimate of the "bias" into account. It is thus divided into two parts. The first part corresponds to creating a model of the registered data to estimate the bias and the second part corresponds to registering the data by subtracting the estimated biases from the computed parameters.

In the ADHD experiments based upon estimation of the T2 relaxation parameter, the estimate of T2 is based on an exponential decay at each point. Essentially, for each x,y,t triplet, where x,y is a pixel position, and t is an echo time estimate, the signal should be of the form $s(x,y,t)=s0(x,y)e^{-t/T2(x,y)}$ where $T2(x,y)$ is the T2 relaxation time for the contents of pixel x,y. To compute the biases, one first needs an estimate of $s0(x,y)$ and $T2(x,y)$. One way to do this is to assume first that there is no motion and go through the equations for T2 and S0 computation.

Once the estimates are computed, one can construct a model data set which would be the "exact" values of s(x,y,t) which would be expected if your estimates were correct. This data set is motion-free in the frame-wise sense, i.e. any motion in the original data used to compute it is "blurred" into the estimates of s0(x,y) and T2(x,y) and, by definition, removed from the t subscript of the model data set since the model data set was created by again assuming no motion.

Passing this model data set through the DART algorithm yields a set of parameters from motion. Since the data have no motion, by definition, this provides an estimate of the "bias" expected in the registration of the real data set. Once the bias parameters are computed for each of the images in the model data set as compared to the model reference frame, these values can be stored as "corrections" to be subtracted away during the second part, the actual registration of the experimental images.

This works wherever there is a reasonable model that can be constructed as to what the data might look like in the absence of motion. For instance, in CBV mapping experiments, there is a dip in signal at each pixel whose area integrated over time is theoretically proportional to the blood volume at each pixel (with certain logarithmic scalings). The problem is that the exact shape of the dip is variable from pixel to pixel and from person to person. It is not unreasonable to assume that for a single person, the waveforms at each pixel, to a scaling factor, are the same. Thus one model involves computing the average waveform in a brain slice and computing the blood volume assuming that there is no motion in the experimental data set (i.e., running the integration directly on the data), and then back-computing a model data set which would yield those exact results.

The process is the same as the T2-mapping model above. Estimate some "global" time-independent or pixel-independent parameters which capture the essence of the data set according to some experimental model of the data using the raw data (not motion corrected), then create a model data set from those global parameters to pass through the motion correction algorithm (which need not be DART of course) to compute estimates of the bias which would be expected from the algorithm for that type of data, then use the bias information to more accurately motion correct the raw data.

Although in a preferred embodiment, this process is carried out once for each experimental data set, it should be clear that such a process might be iterated any number of times or until some stopping criteria were met with the goal of yielding better corrections (since the closer the original data is to perfectly "registered", the more exactly the model data set will match the true data set—assuming the model is right, of course).

Thus, for instance, one might first estimate a set of model parameters from the uncorrected data. Those parameters would be used to create the first model data set. That model data set might be used to estimate the first bias parameters. Those bias parameters might be used to compute the first true motion correction parameters. Those parameters are used to create the first registered data set.

Then a second improved estimate of the model parameters might be computed directly from the first registered data set, leading to a second improved model data set, leading to improved bias parameters. Those bias parameters would be be used to improve the estimates of the registration of the raw data, yielding a second improved registered data set . . . and so forth.

A stopping condition might be when the change in the bias parameters between two iterations becomes unmeasureably small, or a fixed number of iterations is completed, or some amount of time elapses, etc.

It should be appreciated that even fMRI experiments (increasingly popular) have some degree of contrast between images (it is this differing part of the signal which is the data of interest) raising the possibility that the more general model, estimate bias, correct method of image registration may also be better suited to even low-contrast time-varying data.

Continuing now with a description of the flow diagram, once the readings are taken at each point and the motion correction is made, particular regions of interest (ROI) are identified as shown in step 46. One technique for identifying the ROI is discussed below in conjunction with FIG. 3. Briefly, however, in one embodiment the system provides data in the form of an image and the ROI is identified on the image. In some embodiments the ROI is identified by using a CAD system or other device to circle or otherwise indicate on the image the ROI.

In some applications the ROI is selected ahead of time based on empirical data which is available. For example, in cases where a system user is attempting to detect brain dysfunction such as attention-deficit/hyperactivity disorder (ADHD), the ROI may correspond to brain regions such as the striatum (caudate and putamen). It should be noted, however, that to detect other brain dysfunction, it may be desirable to select other brain regions as the ROI. Depending upon the particular application, it may be desirable or necessary to identify more than one ROI. For example, in some cases it may be desirable or necessary to identify two ROIs. Thus, the particular ROI as well as the number of ROIs may be different for different brain dysfunction and more than one ROI may exist for a particular brain dysfunction.

After the ROI is identified, the median pixel intensity values in the ROI are then computed as shown in step 48. In particular, regions of interest with an arbitrary number of pixels, N, are selected. For each of the N pixels, a value of T2 is calculated. The median value (i.e. that value which is greater than half of the other values and also smaller than half of the other values) is selected as the best estimate of T2 for that region of interest. It has been found that the median value of all designated pixels within an ROI provides a regional estimate less susceptible to contamination by spurious values from bordering white matter and cerebrospinal fluid regions than the mean. Thus, regional T2 relaxation time was calculated from the median value of all the designated pixels.

It should be noted that in alternate embodiments, median fitting where the T2 time is first computed at each pixel, and then the median T2 value is used (instead of the median at each pixel being selected, and the T2 being computed from these) can also be used. Those of ordinary skill in the art will appreciate of course that in those instances in which the ROI are tightly grouped, mean values (instead of medians) could also be used in the computation of T2 RT.

Processing then proceeds to step 50 where the T2 RT values are determined from the median pixel values in the ROI. Values of The T2 relaxation time at points x, y denoted as T2(x, y) and values of the signal intensity at points 0, x, y denoted as S(TE=0, x, y) are then calculated on a pixel-wise basis assuming exponential decay. Thus, signals and T2 values for each and every pixel are calculated before a median value for a region of interest is selected. In one embodiment, the calculations are made which may be expressed as:

$\ln S(x,y,n) = \ln S(TE=0) - TE(n)/T2\ (x,y)$ in which:
(x, y) describe the location of the pixel;
n corresponds to the echo number (e.g. a numeric value from 1 to 32); and
S is the image signal intensity.
S(x, y, n) corresponds to the image signal intensity at the pixel located at x, y and at echo number n.

The above equation is used to solve for T2(x,y) by fitting the best line through a data set composed of line S(x,y) for all n TE values.

In one embodiment, a linear least squares regression technique is used to calculate a single T2 relaxation time measure for each pixel (x, y). Those of ordinary skill in the art will appreciate that other linear fitting methods may also be used.

Next, as shown in step 52, the T2 RT is provided to the user for further processing. In one embodiment, the T2 RT of the subject can be compared with a baseline T2 RT. Based on such a comparison, a determination of whether a subject has ADHD can be made.

Figure 3:
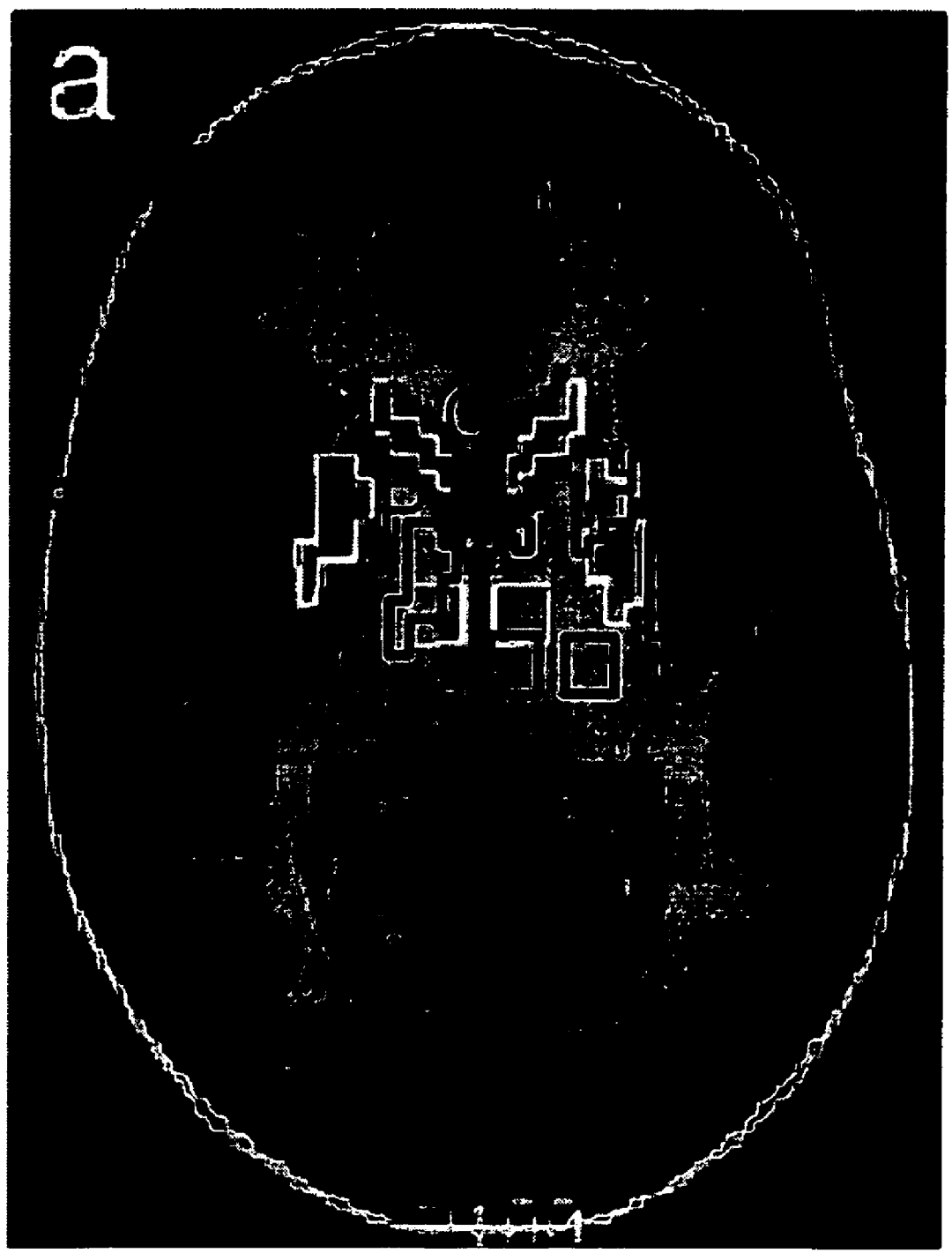
FIG. 3 is a top view of an MRI image.

Referring now to FIG. 3, a T1 weighted brain image is shown. The regions of interest (ROIs) are identified by using anatomic boundaries observed in the T1 weighted image. The ROIs is identified by circumscribing a particular brain region shown in the T1 weighted image. As shown in FIG. 3, the putamen P, the caudate C and the thalamus T are all circumscribed on both the left and right sides of the brain image. It should be noted that each ROI is conservatively circumscribed to thus avoid encroaching into ventricular space. It should be appreciated that the general concept is to try and define regions of interest which are as homogeneous as possible. Thus, it is desirable to avoid partial volume effects arising from the erroneous inclusion of CSF in ROI, for example.

Calculations of regional T2 relaxation time were made for left and right anterior caudate, putamen and thalamus (as a contrast region) using the circumscribed portions of the appropriate anatomic boundaries shown in FIG. 3.

In studies, delineation of regions and analysis of imaging data was performed on coded images, and the responsible researcher was blind to the identity, diagnosis, or treatment condition of the subject. It has been found that the median value of all designated pixels within the ROI provides a regional estimate less susceptible to contamination by spurious values from bordering white matter and cerebrospinal fluid regions than the mean. Thus, regional T2 relaxation time was calculated from the median value of all the designated pixels and a plot of the T2 RT for the left putamen is shown in FIG. 3A.

Figure 3A:
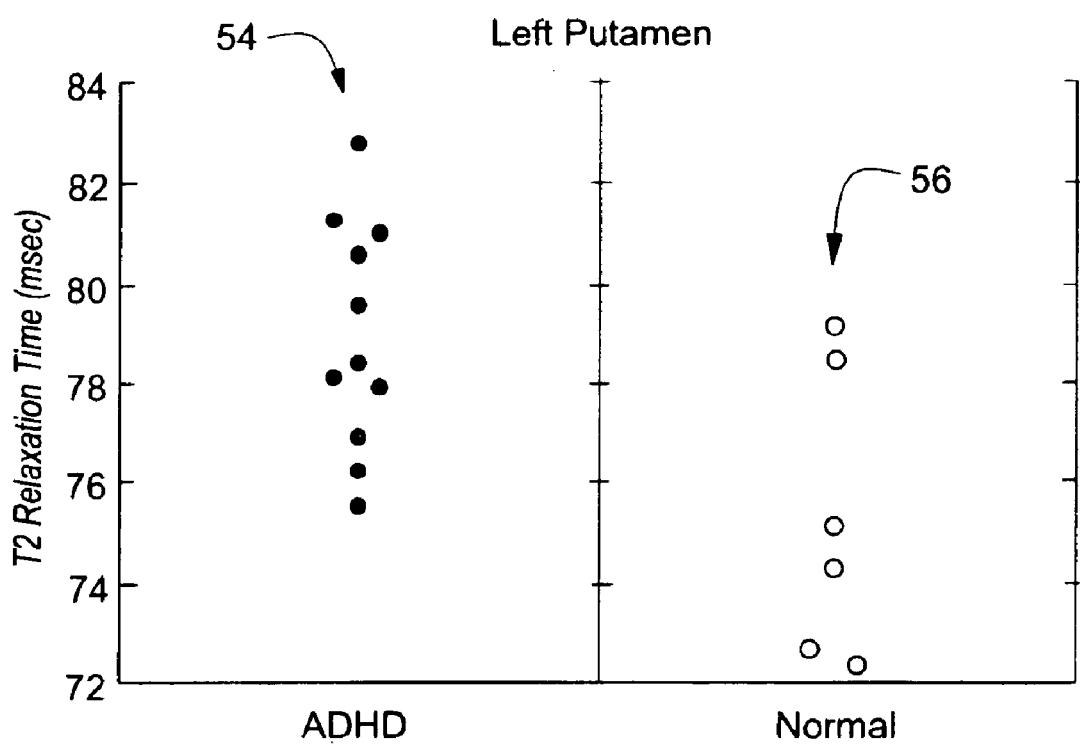
FIG. 3A is a plot of the T2 relaxation times for and a person having attention-deficit/hyperactivity disorder (ADHD) and for a person not having ADHD.

Referring now to FIG. 3A, points 54 correspond to a T2 relaxation time in an ADHD subject while point 56 correspond to a T2 relaxation time in a non-ADHD subject. As can be observed from FIG. 3A, a majority of the T2 relaxation times in the non-ADHD subject are below the T2 relaxation times in the ADHD subject.

It should be noted that while in one embodiment described herein, the putamen was found to correspond to a brain region useful for diagnosing ADHD, after reading the description of the invention provided herein, those of ordinary skill in the art will now appreciate that other brain regions may also be useful for diagnosing ADHD. It should also be appreciated that the apparatus and techniques of the present invention may be applied to other brain regions and that examination of T2 RT in other brain regions may be useful for diagnosing conditions other than ADHD.

It should also be noted that by reliably measuring the T2 RT in a particular region of interest in a subject it may be possible to provide a non-invasive technique for assisting in the diagnoses of a variety of diseases including but not limited to ADHD, Asperger's syndrome, Autism, substance abuse disorders, seasonal affective disorder, childhood sexual abuse, schizophrenia, manic depression, Alzheimer's disease, Parkinson's disease and compulsive disorders. It would be necessary to determine which region or regions of the brain or provide a detectable change in response to the particular disease or disorder of interest.

Figure 4:
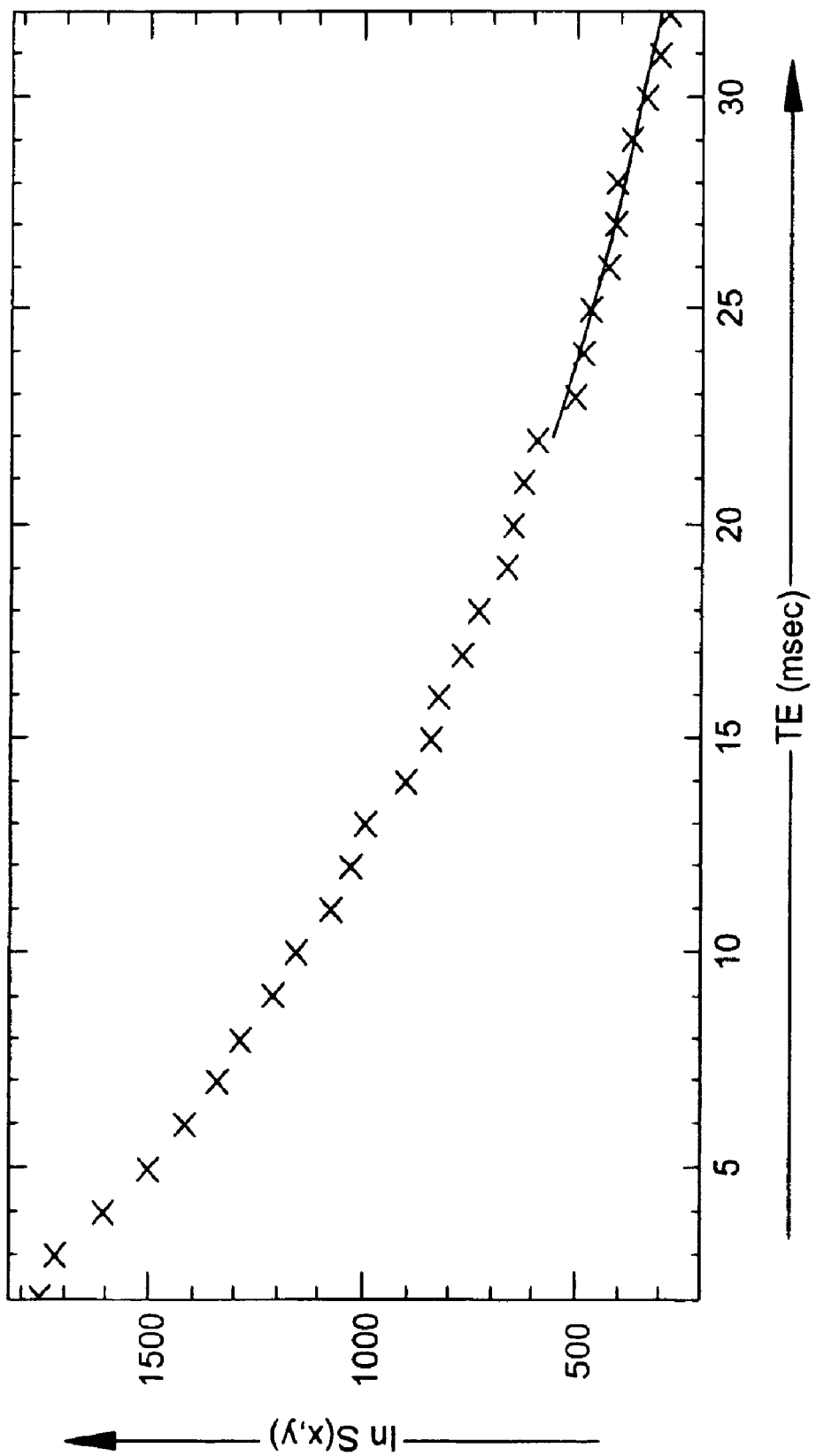
FIG. 4 is a plot of the T2 relaxometry based on median values of pixels in a region of interest.

Referring now to FIG. 4, a plot of T2 relaxometry computed using the technique described above in conjunction with FIG. 2 is shown. The plotted values correspond to actual data for each observation as described in the poster presentation entitled: Methylphenidate Dose-Dependent Effects of Methylphenidate on Activity, Attention and Magnetic Resonance Measures in Children with ADHD which reference is hereby incorporated by reference in its entirety.

Figure 5:
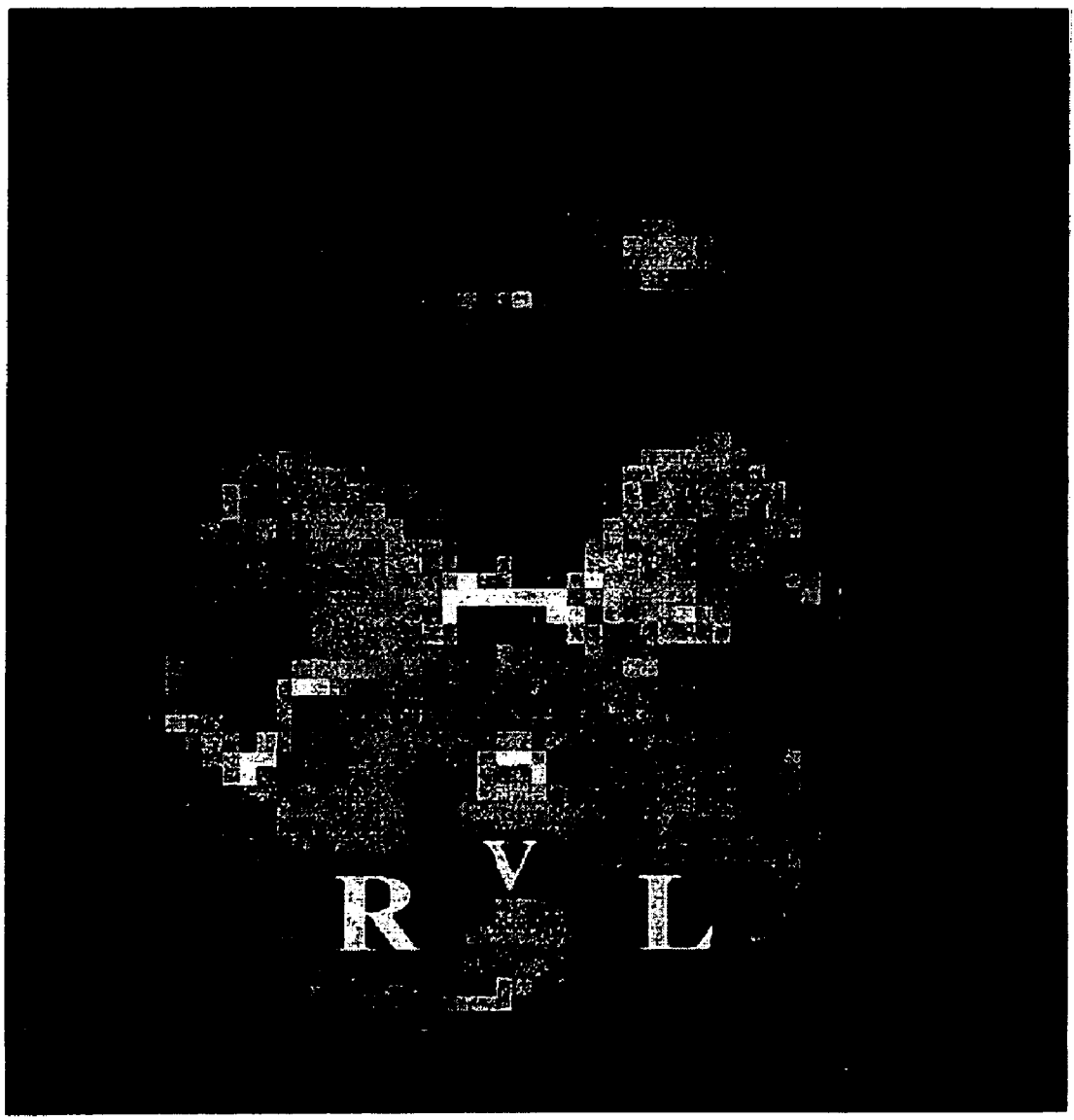
FIG. 5 is an image of the cerebellum of ADHD subjects having regions of interest identified.

Referring now to FIG. 5, a T2 relaxation time image of the brain and cerebellum is shown. Circumscribed ROIs are illustrated for the cerebellar vermis V as well as, right R and left L cerebellar hemispheres. The cerebellar vermis is an anatomical region of the cerebellum where lesions have been found in ADHD children. The cerebellar hemispheres were chosen as contrast regions.

Figure 6:
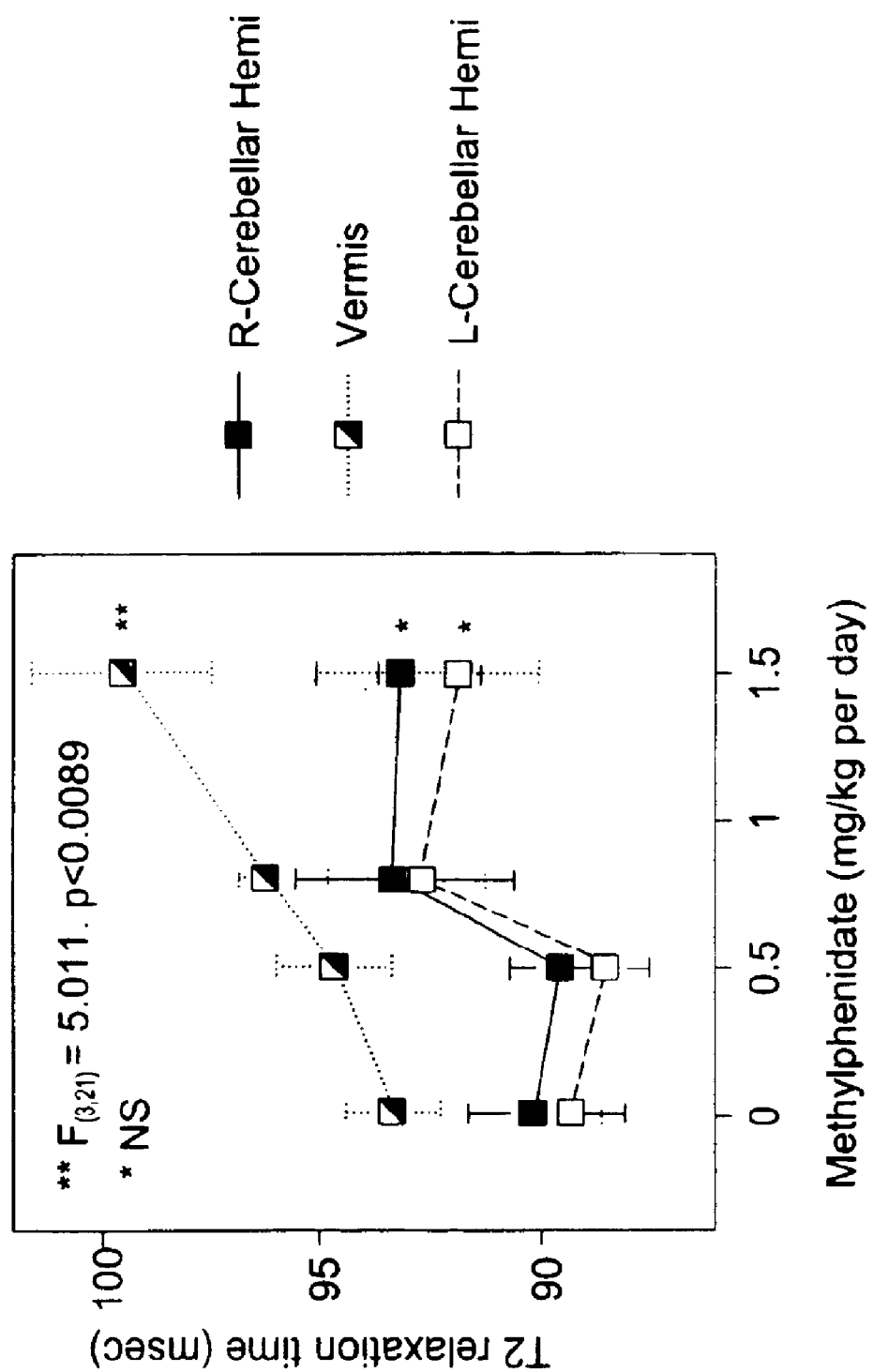
FIG. 6 is a plot of T2 relaxation time vs. Methylphenidate dose showing dose-dependent changes in cerebellar blood flow.

Referring now to FIG. 6, a plot of T2 relaxation time vs. Methylphenidate illustrates dose-dependent changes in the cerebellar blood flow. This plot shows that drug effects can be monitored with T2 relaxometery.

In another aspect of the invention, fMRI imaging is used to determine an optimal drug dosage to treat a disorder, such as ADHD. An objective determination is made for a patient regarding the presence and/or level of a physiological condition, e.g., ADHD. The patient is given a drug in varying doses to treat the physiological condition. Subsequently, fMRI imaging is used to determine the effects of the drug in relation to dosage to ascertain the optimal drug dosage for the patient.

In one embodiment, functional magnetic resonance imaging (fMRI), which is described above in detail, is used to test the effects of methylphenidate (MPH) on steady-state blood volume in the midline vermis of the cerebellum in boys with Attention-Deficit/Hyperactivity Disorder (ADHD). As is recognized by those skilled in the art, this region of the brain is significantly smaller in children with ADHD. In addition, the vermis has been shown to modulate forebrain dopamine systems, to influence locomotor activity, and to contain a significant density of dopamine transporters.

In one particular embodiment, T2 relaxometry was used to indirectly assess blood volume in the cerebellum (hemispheres and midline vermis) of ten ADHD boys treated continuously for one week with placebo and three different doses of MPH. It was found that T2 relaxation time (T2-RT) values are inversely proportional to local cerebral blood volume. Following each week of treatment, and within 1–3 hours of their afternoon dose, testing for drug efficacy was performed using objective measures of activity.

The results indicate that moderate and high doses of MPH increased T2-RT in a rate-dependent manner increasing T2-RT in the most active ADHD children, and reducing T2-RT in ADHD subjects who were not objectively hyperactive.

Before describing the invention in further detail, some ADHD information is now presented for facilitating a more complete understanding of the invention. Conventional neurobiological theories of ADHD have predominantly focused on the prefrontal cortex and the basal ganglia. This would appear logical given the association of frontal lobe hypofunction with impulsive behavior, working memory and "executive" function deficits. The basal ganglia are well known to be involved in the regulation of locomotor activity, and both regions are primary targets of the ascending dopamine (DA) system, which is directly affected by stimulant medications. However, morphometric studies of ADHD children have consistently found that both boys and girls with ADHD have reduced size of the posterior-inferior lobules of the cerebellar vermis. This is interesting as the cerebellum receives DA projections from the ventral tegmental area (VTA) and the posterior-inferior lobules of the cerebellar vermis have the highest concentration of DA transporters in the primate vermis. Further, there are reciprocal loops that interconnect a large and diverse set of cerebral cortical areas, including the prefrontal cortex with the basal ganglia and cerebellum by way of the pons, dentate nucleus, and thalamus. The vermis, through its fastigial projections to the VTA and locus coeruleus, exerts strong effects on the turnover of DA and noradrenaline (NA) in the caudate and nucleus accumbens. Stimulation of the hook bundle, a projection pathway in the white matter of the cerebellum, containing fibers from the caudal-fastigial nucleus that receives direct Purkinje cell efferents from the posterior-inferior vermis, elicits locomotor activity in the decerebrate cat.

As described below, the effects of methylphenidate on the cerebellar vermis of children with ADHD can be assessed using T2 relaxometry (T2-RT) by ascertaining changes in steady-state blood flow with chronic drug administration. Based upon the T2-relaxometry results, an optimal drug dosage for an individual can be determined. That is, blood flow to the cerebellar vernis can be titrated to a normal range by administering the corresponding drug dosage.

It is known that daily treatment with high-dose methylphenidate changed T2-RT in the putamen, supporting the link between dysfunction in cortico-striatal-thalamic circuits and the capacity to inhibit motor activity and sustain attention. Although stimulants are known to exert robust effects on catecholamine systems, imaging studies have often failed to reveal reproducible medication effects. For example, in the article Matochik J A, Liebenauer L L, King A C, Szymanski H V, Cohen R M, Zametkin A J: *Cerebral glucose metabolism in adults with attention deficit.hyperactivity disorder after chronic stimulant treatment*. Am. J. Psychiatry 1994; 151(5):658–64, found no consistent effect of chronic methylphenidate or dextroamphetamine on regional brain metabolism of adult ADHD patients using PET. Similarly, Ernst M, Zametkin A J, Matochik J A, Jons P H, Cohen R M: *DOPA decarboxylase activity in attention deficit hyperactivity disorder adults. A [fluorine-18] fluorodopa positron emission tomographic study*. J. Neurosci. 1998; 18(15):5901–7, found no consistent effect of i.v. dextroamphetamine on global or regional metabolic rates of adult ADHD subjects, even though the drug produced robust effects on attention. Global metabolic rate changed substantially in most patients after treatment, but in both directions. Volkow N D, Wang G J, Fowler J S, Logan J, Angrist B, Hitzemann R, Lieberman J, Pappas N: *Effects of methylphenidate on regional brain glucose metabolism in humans: relationship to dopamine D2 receptors*. Am. J. Psychiatry 1997; 154(1):50–5, found that methylphenidate increased frontotemporal metabolism in subjects with high availability of DA D2 receptors and decreased metabolism in subjects with low availability of D2 receptors.

Significantly, and in accordance with the present invention, the magnitude and direction of methylphenidate effects on T2-RT in the putamen were highly dependent on the subject's hyperactivity (capacity to sit still off medication), which is related to individual differences in DA receptor density or function. In an exemplary embodiment, fMRI investigation was coupled with objective laboratory assessment of the child's capacity to sit-still and pay attention on placebo and during treatment with low, intermediate and high doses of methylphenidate.

EXAMPLE

Ten boys with ADHD (9.3±1.6 yr), and six healthy comparison subject boys (10.2±1.5 yr) were studied. Children with ADHD were screened using structured diagnostic interview (the Schedule for Affective Disorders and Schizophrenia for School-Age Children—Epidemiologic Version, "K-SADS-E") and included if they met criteria for ADHD, and had at least 6 of 9 symptoms of inattention or hyperactivity-impulsivity. Children then took part in a triple blind (parent, child, rater), randomized, placebo-controlled study on the effects of methylphenidate (0, 0.5, 0.8, 1.5 mg/kg/day in two divided doses) on activity and fMRI. Children were treated continuously for one week with placebo or specific dose of methylphenidate. They were tested on day seven for drug response using objective measures of activity immediately following fMRI.

On test days, parents were instructed to give the afternoon dose 1 hour prior to their MRI appointment. Medication administration was assessed at each visit to insure that time between ingestion and testing were held constant for each subject throughout the study. Within each subject there was an average of 28 minutes of variation in MRI start times between the different dose conditions. Objective assessment of attention and activity followed MRI by an average of 42±39 minutes.

Images were acquired using a 1.5-T magnetic resonance scanner (Signa, General Electric Medical Systems, Milwaukee, Wis.) equipped with a whole-body, resonant gradient set capable of echo planar imaging (Advanced NMR Systems, Inc., Wilmington, Mass.), and a standard quadrature head coil for image detection. During each examination, 3 categories of images were obtained: (1) Scout images (typically T1-weighted sagittal images); (2) High resolution T1 matched axial images through the ten planes for which maps of T2 were generated; and (3) 32 spin echo, echoplanar image sets, with TE incremented by 4 msec in each consecutive image set (e.g. TE (1)=32 msec, TE (2)=36 msec, . . . TE (32)=156 msec) through the same ten axial planes (TR=10 msec, Slice thickness=7 mm with a 3 mm skip, in-plane resolution=3.125 mm×3.125 mm, FOV= 200 mm). The 32 TE-stepped images were then transferred to an off-line workstation and corrected for in plane motion using a modification of the DART image registration algorithm.

The DART algorithm provided vertical, horizontal and rotational values for subject movements during each functional scan. These values, which were within the range for which the registration algorithm has been validated, were significantly different between ADHD subjects and comparison subjects for horizontal and vertical movement on ANOVA (analysis of variance), (x-axis, F=8.33, df=1, 14, p=0.01; y-axis, F=9.07, df=1, 14, p=0.01. There was no difference for ADHD subject movements as a function of methylphenidate dose (F=1.97, df=3,21, p=0.15). For example, average head movement (SD) in the maximal vertical direction for ADHD boys on placebo was 1.16±0.84 mm, 1.66±1.62 mm after high dose methylphenidate and 0.12±0.05 mm for comparison subjects.

Values of T2 (x, y) and S (TE=0, x, y) were then calculated on a pixel-wise basis, assuming exponential decay, i.e. ln [S (x, y, n)]=ln [S (TE=0), x, y]−TE (n)/T2 (x, y) where (x, y) describe the location of the pixel; n characterizes the echo number, from 1 to 32; and S is the image signal intensity. Linear least-squares regression was used to calculate a single T2 relaxation time measure for each pixel (x, y). Calculations of regional T2 relaxation time were made for regions of interest (ROI) drawn manually under the guidance of conventional T1-wighted matched MRI images in 2 to 4 slices through the cerebellum using anatomic boundaries observed in T1-weighted, preliminary T2-RT maps, and an atlas of the cerebellum. ROI slice selections were based on an assessment of the presence of cerebral spinal fluid in order to minimize partial volume artifacts, which result in abnormally elevated T2 relaxation times (values>100 msec were rejected). Sixteen voxel ROI's in the vermis were conservatively limited to square regions (X=6 mm by Y=6 mm), to avoid encroaching into ventricular space and to provide consistency between slices and subjects.

FIGS. 7A and 7B show representative cerebellar ROIs including the vermis V and the left and right cerebella C. Delineation of regions and analysis of imaging data were performed on coded images, by an analyst very familiar with cerebellar anatomy who was blind to the identity, diagnosis, and treatment condition of the subject. The coefficient for intra-rater reliability, $\alpha$ was 0.987 based on four separate and independent T2 relaxation time measures from the vermis of seven subjects. Regional T2 relaxation times were calculated from the median value of all the designated pixels, as the median provides a regional estimate less susceptible to contamination by spurious values from cerebrospinal fluid than does the mean. Regional T2-RT values were averaged for all slices within subjects and differences between placebo and drug conditions were then calculated.

To accurately gauge the effects of methylphenidate on cerebellar blood flow, prior to scanning, individual differences in the ability to sit still and pay attention were precisely assessed. An exemplary objective procedure was used in which subjects were challenged to attend to a monotonous but demanding computerized continuous performance task (CPT) during which head movements were recorded using infrared motion analysis. The optical tracking system recorded fidgeting-induced vertical and horizontal displacements of a reflective head marker to a resolution of 0.04 mm. Measures of immobility were derived from marker movement by calculating the average time between movements during the fifteen minute test. A movement was defined to occur whenever the marker moved >1 mm from the position of the previous movement.

Objective systems for evaluating potentially ADHD patients are well known to one of ordinary skill in the art. One such system is the OPTAx™ (Optical Tracking and Attention Test) by OPTAx™ SYSTEMS, Inc. of Burlington, Mass.

Analysis of cerebellar or vermal T2-RT failed to reveal any significant effect of dose with repeated-measures ANOVA (F=1.167,df=3, 27, p=0.34). Some subjects had an increase in T2-RT and others had a decrease. However, the magnitude and direction of change varied directly with each subject's degree of hyperactivity when unmedicated based upon the objective test results, e.g., the Optax test result. Analysis of covariance with motor activity revealed a robust effect of methylphenidate treatment on vermal T2-RT (F=4.85, df=3, 24, p=0.009), along with a significant dose× activity interaction (F=3.90, df=3, 24, p=0.02). Further, the effect of dose was linear (F=15.14, df=1, 8, p=0.005). No effect of methylphenidate treatment was observed on T2-RT in the adjacent cerebellar hemispheres (Dose, F=0.88, df=3, 21, p>0.4; Dose×Activity, F=0.47, df=3, 21, p>0.7).

Figure 8A:
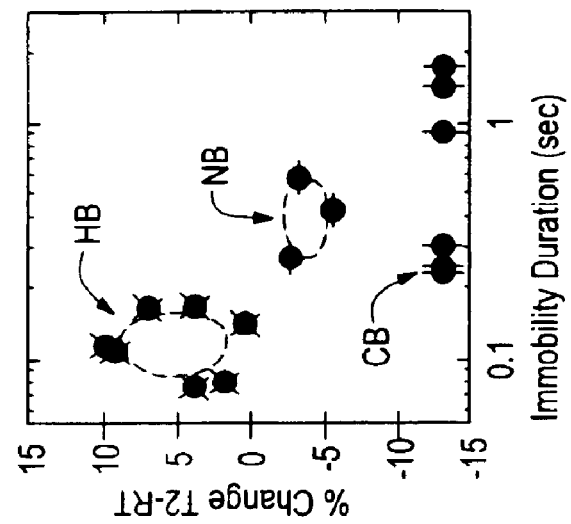
FIG. 8A is a graphical depiction of a first dose versus percentage change in T2-RT as a function of basal activity for patients treated in accordance with the present invention.
Figure 8B:
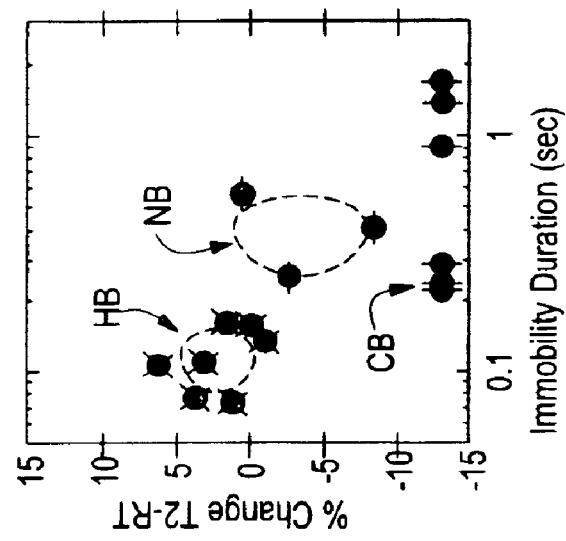
FIG. 8B is a graphical depiction of a second dose versus percentage change in T2-RT as a function of basal activity for patients treated in accordance with the present invention.
Figure 8C:
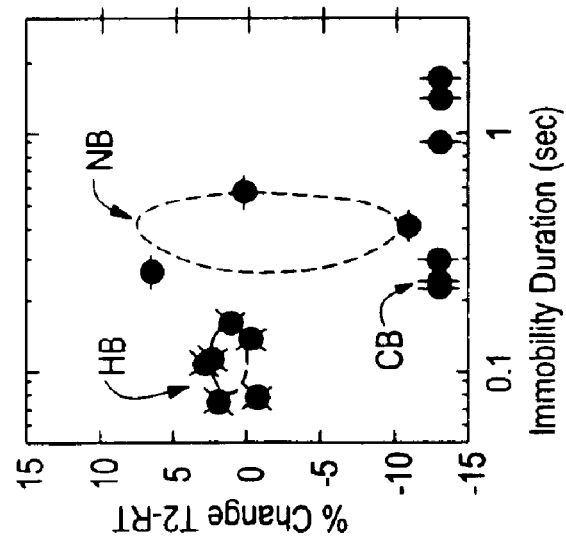
FIG. 8C is a graphical depiction of a third dose versus percentage change in T2-RT as a function of basal activity for patients treated in accordance with the present invention.

FIGS. 8A–C show the percentage change in cerebellar vermis T2-RT for low dose (FIG. 8A), intermediate dose (FIG. 8B), and high dose (FIG. 8C) of methylphenidate (relative to placebo) as a function of basal activity determined by the average amount of time spent sitting still on placebo. The immobility duration is in seconds for a $\log_{10}$ scale. In each figure, the percent change is shown for (seven) hyperactive boys HB, (three) non-hyperactive boys NB, and (six) comparison boys CB. The hyperactive boys HB spent at least twenty percent less time sitting still than the most active comparison subject.

The low dose resulted in a non-significant group effect (F=0.63, df=1, 8, p=0.63), the intermediate dose resulted in a significant group effect (F=6.75, df=1, 8, p=0.04), and the high dose resulted in a significant group effect (F=15.98, df=1, 8,p=0.004). Boys who spent the least time sitting still (e.g., who were the most hyperactive) demonstrated a positive dose-dependent change in T2-RT. A negative dose-dependent change in T2-RT was observed in boys who sat still longer. Vermal T2-RT increased 1.2%, 2.1% and 5.1% at low, intermediate, and high doses, respectively, in the seven boys who were at least 20% more active than the most active comparison subject.

In contrast, T2-RT decreased an average of 1.3, 3.5 and 3.9% in the three least active boys with ADHD. As can be seen, percent changes in T2-RT for hyperactive and non-hyperactive boys were significantly different by repeated measures ANOVA for intermediate and high doses but not low doses of methylphenidate. There was no significant association between percent change in T2-RT and percent change in activity with methylphenidate. However, at the highest dose tested there was a modest correlation (Pearson r=0.45, df=8, p=0.19), which would have been significant if an apparent outlying point was eliminated (r=0.721, df=7, p=0.02). As is well known to one of ordinary skill in the art, the Pearson product moment test is a measure of correlation. There was a significant association between the objective measures of time spent immobile on placebo and number of DSM-IV (Diagnostic and Statistical Manual of Mental Disorders—Fourth Edition) symptoms of hyperactivity reported during clinical interview (r=0.72, df=10, p=0.01). However, clinical ratings of activity was a weak covariate which failed to reveal a significant effect of methylphenidate on T2-RT (F=0.66, df=3,23, p>0.5).

The highest dose of methylphenidate produced, on average, a 5.1% increase in T2-RT in the ADHD children who were objectively hyperactive, and a 3.9% reduction in T2-RT in the three ADHD children who were not. While the percentage changes may appear to be small, they are quite strong and correspond to an effect size (Cohen d) of 2.13 (95% CI, 0.82–3.44) in the hyperactive subjects. An independent measures form of Cohen's d was used to calculate effect sizes. Sample sizes were then incorporated into confidence intervals using 95% limits±the standard deviation calculated using the method given by Hedges and Olkin (1985, p. 86) *Statistical Methods for Meta-Analysis*. New York: Academic Press, for the medication-induced changes in T2-RT.

A linear regression relationship between vermal T2-RT and relative cerebral blood volume (rCBV) has been established using dynamic susceptibility contrast magnetic resonance imaging in nine healthy 18–22 year-old young adults under resting conditions. Vermal rCBV values ranged from 0.7–2.0 (arbitrary units) while T2-RT ranged from 90–95.5 msec. Hence, a 4 msec change in T2-RT may be associated with a very marked change in rCBV. Precise estimation of rCBV changes should not be inferred, as this correspondence was observed in unmedicated adults and not medicated children, but it does suggest that this degree of change in T2-RT should be associated with a biologically important change in rCBV.

Thus, methylphenidate exerts a robust dose-dependent effect on the paramagnetic properties of the cerebellar vermis resulting from alterations in regional blood flow and volume. However, both the magnitude and direction of the effects were entirely dependent on the subject's basal level of hyperactivity or capacity to sit still. Failure to incorporate this intervening variable in the analysis completely obscured the effect. This may help to explain why previous efforts have failed to find consistent effects of methylphenidate or dextroamphetamine on regional brain metabolism.

Figure 9:
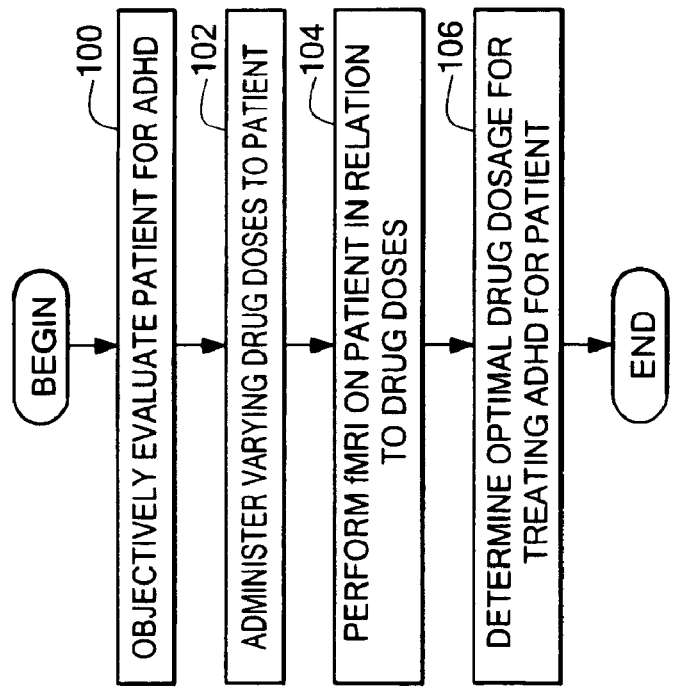
FIG. 9 is a flow diagram showing an exemplary sequence of steps for treating an ADHD patient in accordance with the present invention.

FIG. 9 shows an exemplary sequence of steps for treating ADHD in accordance with the present invention. In step 100, a behavioral assay is performed on a patient to obtain an objective assessment of the presence and level of ADHD in the patient. A drug, such as methylphenidate is then administered to the patient at varying doses in step 102. It is understood that the dosages can vary in granularity based upon a desired level of dose optimization. In step 104, an fMRI is performed on the patient in time relation to administration of the drug. The fMRI can be performed and the results analyzed as described in detail above. Based upon the fMRI results, an optimal drug dose can be determined based upon the individual's response to the varying drug doses.

Figure 10:
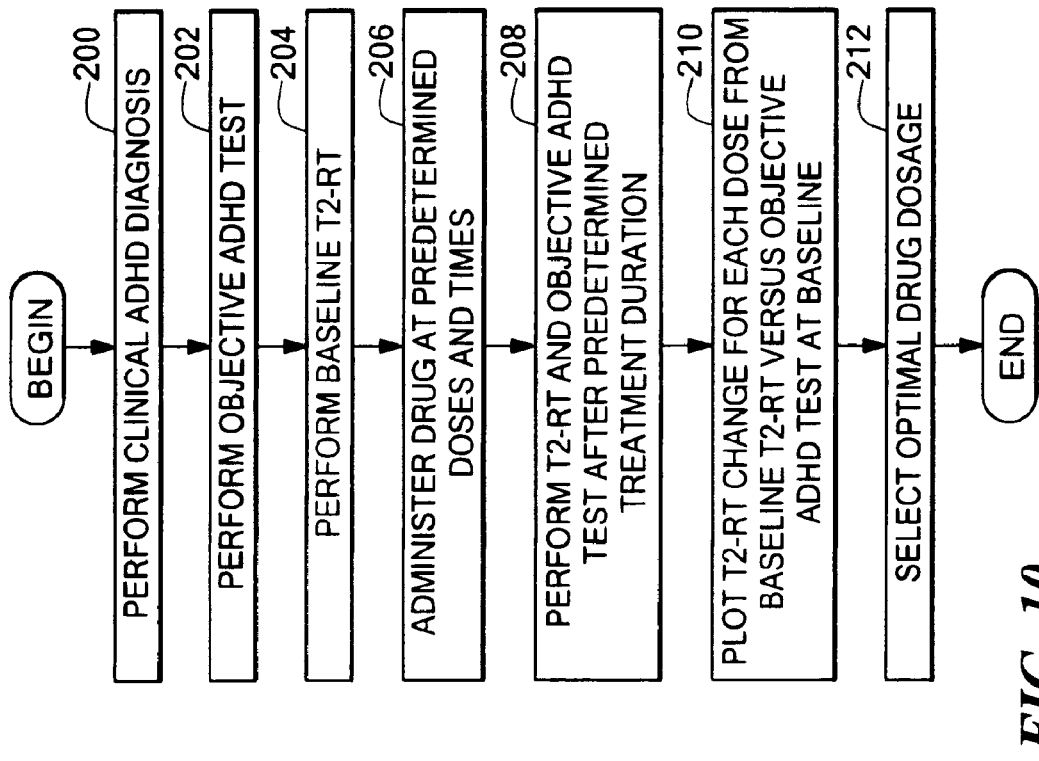
FIG. 10 is a flow diagram showing an exemplary sequence of steps for determining an optimal drug dose for ADHD treatment in accordance with the present invention.

FIG. 10 shows an exemplary sequence of steps for determining an optimal drug dosage for an ADHD patient in accordance with the present invention. In step 200, a patient is clinically examined for ADHD, such as by determining the number of DSM-IV symptoms. In one embodiment, an ADHD determination requires finding 6 of 9 symptoms of inattention or hyperactivity. In step 202, an objective test of ADHD level is performed on the patient, such as the Optax test. The Optax test can provide a determination of immobility duration at baseline, which can be compared with an age-based normal range.

In step 204, an fMRI is performed to obtain a baseline brain T2-RT, which is described in detail above. A predetermined drug dose is then administered to the patient at scheduled times in step 206. In one particular embodiment, methylphenidate is administered in doses of 0.5, 0.8, or 1.5 mg/kg per day in two divided doses for a week. In step 208, an fMRI is performed on the patient to determined a brain T2-RT and immobility duration is evaluated at predetermined times for the specified dose. In an exemplary embodiment, the fMRI and the objective ADHD test are administered about one hour following the last dose (after the week). The fMRI and Optax test can be performed for each dose.

In step 210, changes in the brain T2 RT at each dose from the baseline T2 RT can be plotted against the objective immobility duration test at baseline. In step 212, the dose having the largest positive percent change in T2 from the baseline can be selected for optimal treatment of the patient.

Various modifications to the above-described treatment will be readily apparent to one of ordinary skill in the art, including, for example, drug dose changes, dose administration times, testing times, and the like.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for treating attention deficit/hyperactivity disorder (ADHD), comprising:
   performing an objective ADHD behavioral assay for a patient;
   administering a drug to the patient at varying doses; and
   performing an fMRI on the patient for the varying drug doses to determine an optimal dosage for the patient.

2. The method according to claim 1, further including performing a further objective ADHD behavioral assay after the drug administration.

3. The method according to claim 1, further including performing the objective ADHD behavioral assay using monotonous computerized task.

4. The method according to claim 1, further including performing the objective ADHD behavioral assay using an Optax test.

5. The method according to claim 1, further including administering methylphenidate to the patient.

6. The method according to claim 1, further including performing the fMRI to obtain T2 RT information to assess blood volume changes in a cerebellum of the patient in response to the drug doses.

7. The method according to claim 6, further including selecting a first one of the varying drug doses based upon blood flow levels to the cerebellar vermis of the patient in response to the drug doses.

8. The method according to claim 1, further including performing the fMRI at predetermined times after the administration of the drug.

9. The method according to claim 1, further including screening the patient by evaluating the patient for a predetermined number of ADHD symptoms.

10. The method according to claim 1, further including obtaining a baseline fMRI for the patient.

11. The method according to claim 1, further including administering each of the varying drug doses for about a week.

12. The method according to claim 1, further including plotting a T2 RT change for each of the drug doses from a baseline T2 RT.

13. The method according to claim 12, further including plotting the T2 RT changes versus a baseline objective ADHD test of the patient.

14. The method according to claim 12, further including selecting the optimal one of the varying drug doses corresponding to a largest positive percent change in the T2 RT from baseline.

15. The method according to claim 1, further including
   identifying a region of interest (ROI) in the fMRI;
   computing median pixel intensity values in the ROI; and
   determining a T2 relaxation time from the median pixel intensity values.

16. A method for selecting an optimal drug dosage to treat ADHD, comprising:
   performing a first objective ADHD test on a patient;
   performing an fMRI on the patient to obtain a baseline T2 RT in the cerebellum;
   administering a drug to the patient at a first dosage for a first period of time;
   performing an fMRI on the patient to obtain T2 RT information including blood flow changes in the cerebellum in response to the first dosage;

performing a second objective ADHD test on the patient a known time after the administration of the first dose;

administering the drug to the patient at a second dosage for a second period of time;

performing an fMRI on the patient to obtain T2 RT information including blood flow changes in the cerebellum in response to the second dosage;

performing a third objective ADHD test on the patient a known time after administration of the second dose; and selecting the first or second drug dose to treat ADHD based upon a level of T2 RT change for each of the first and second doses from the baseline T2 RT versus the first objective ADHD test.

17. The method according to claim 16, further including administering methylphenidate as the drug.

18. The method according to claim 16, further including performing the fMRI for the first dosage after the first predetermined time.

19. The method according to claim 16, further including the first objective ADHD test as an Optax test.

* * * * *

UNITED STATES PATENT AND TRADEMARK OFFICE
CERTIFICATE OF CORRECTION

PATENT NO.     : 6,898,455 B2
DATED          : May 24, 2005
INVENTOR(S)    : Anderson et al.

It is certified that error appears in the above-identified patent and that said Letters Patent is hereby corrected as shown below:

Column 1,
Line 66, delete "spin-echo the" and replace with -- spin-echo, the --.
Line 67, delete "expressed" and replace with -- expressed: --.

Column 2,
Line 17, delete "spin echo" and replace with -- spin-echo --.
Line 24, delete "pulse a signal" and replace with -- pulse, a signal --.

Column 3,
Line 39, delete "provide technique" and replace with -- provide a technique --.

Column 4,
Line 2, delete "subject it may" and replace with -- subject, it may --.

Column 5,
Lines 24-25, delete "in putamen" and replace with -- in the putamen --.
Line 43, delete "in caudate" and replace with -- in the caudate --.

Column 6,
Line 25, delete "for and a" and replace with -- for a --.

Column 7,
Line 26, delete "seasonal affective disorder," and replace with -- seasonal affective disorders, --.
Lines 39-40, delete "amplifier provides" and replace with -- amplifier 20 provides --.
Line 53, delete "in the region 19." and replace with -- in region 19. --.

Column 8,
Line 3, delete "provided for example" and replace with -- provided, for example, --.

Column 9,
Lines 55 and 63, delete "spin echo," and replace with -- spin-echo; --.

Column 11,
Line 50, delete "is to perfectly "registered,"" and replace with -- is to be perfectly "registered," --.
Lines 63-64, delete "would the be" and replace with -- would then be --.

UNITED STATES PATENT AND TRADEMARK OFFICE
CERTIFICATE OF CORRECTION

PATENT NO. : 6,898,455 B2
DATED : May 24, 2005
INVENTOR(S) : Anderson et al.

It is certified that error appears in the above-identified patent and that said Letters Patent is hereby corrected as shown below:

<u>Column 14,</u>
Lines 14-16, delete "entitled: Methylphenidate... ADHD which" and replace with
-- entitled: Methylphenidate…ADHD, which --.

<u>Column 15,</u>
Line 8, delete "reduced size" and replace with -- reduced the size --.

<u>Column 16,</u>
Line 23, delete "or specific" and replace with -- or a specific --.

<u>Column 17,</u>
Line 10, delete "T1-wighted" and replace with -- T1-weighted --.
Line 48, delete "marker movement" and replace with -- marker movements --.

Signed and Sealed this

Twenty-first Day of March, 2006

JON W. DUDAS
*Director of the United States Patent and Trademark Office*